United States Patent
Grass et al.

(10) Patent No.: US 6,996,204 B2
(45) Date of Patent: Feb. 7, 2006

(54) SEQUENTIAL COMPUTED TOMOGRAPHY METHOD

(75) Inventors: Michael Grass, Hamburg (DE); Thomas Köhler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1 day.

(21) Appl. No.: 10/503,754

(22) PCT Filed: Jan. 30, 2003

(86) PCT No.: PCT/IB03/00314

§ 371 (c)(1),
(2), (4) Date: Aug. 5, 2004

(87) PCT Pub. No.: WO03/065894

PCT Pub. Date: Aug. 14, 2003

(65) Prior Publication Data

US 2005/0147202 A1     Jul. 7, 2005

(30) Foreign Application Priority Data

Feb. 7, 2002  (DE) ............................... 102 04 926

(51) Int. Cl.
*A61B 6/03* (2006.01)

(52) U.S. Cl. .............................. 378/4; 378/15; 378/901
(58) Field of Classification Search ................. 378/4, 378/8, 15, 19, 901
See application file for complete search history.

(56) References Cited

U.S. PATENT DOCUMENTS

| 4,670,892 A | 6/1987 | Abele et al. |
| 6,426,989 B2 | 7/2002 | Grass et al. |
| 6,459,754 B1 * | 10/2002 | Besson et al. ................ 378/4 |
| 2001/0031032 A1 | 10/2001 | Proksa |
| 2004/0022365 A1 * | 2/2004 | Patch ........................ 378/210 |

FOREIGN PATENT DOCUMENTS

EP         1 295 560 A2    3/2003

* cited by examiner

*Primary Examiner*—David V Bruce
(74) *Attorney, Agent, or Firm*—Thomas M. Lundin

(57) ABSTRACT

The invention relates to a computed tomography method in which an examination zone is irradiated from two mutually offset, preferably circular trajectories. In an intermediate region the absorption distribution is reconstructed by means of measuring values from both trajectories, the weight with which the measuring values are used being larger as the distance between the voxel to be reconstructed and the relevant trajectory is smaller.

7 Claims, 5 Drawing Sheets

SEQUENTIAL COMPUTED TOMOGRAPHY METHOD

Figure 1:
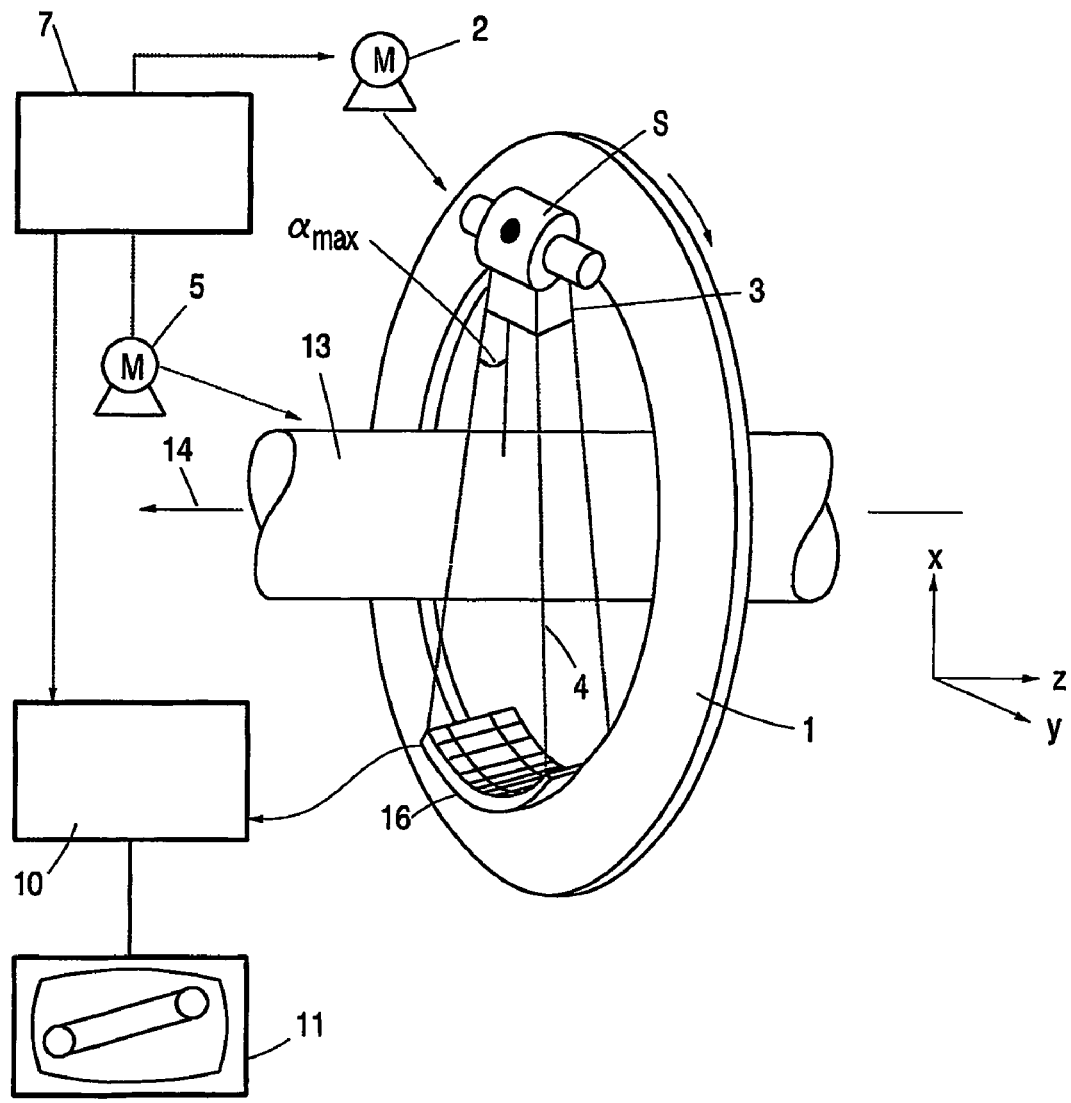

The invention relates to a computed tomography method in which an examination zone is irradiated by a conical radiation beam along a first circular trajectory, and subsequently along a second trajectory which has been offset relative to the first trajectory. The invention also relates to a computed tomography apparatus for carrying out this method as well as to a computer program for controlling such a computed tomography apparatus.

A method of the kind set forth is known from EP 1180251 (=PHDE000070). On the basis of the measuring data acquired therein by means of a suitable detector unit, the variation in space of the absorption or the attenuation of the radiation can be reconstructed in the part of the examination zone which is bounded by the planes defined by the two trajectories. When the distance between these trajectories is suitably chosen, for each voxel in this part of the examination zone there are obtained beams which irradiate the relevant voxel from a total projection angle range of 360°, said beams emanating either from only one of the two trajectories or from both trajectories, depending on the position of the relevant voxel. This enables a reconstruction with a signal-to-noise ratio which is higher than would be the case if only beams from a projection angle range of 180° (being adequate per se) were used. However, artifacts are liable to occur, which artifacts are more pronounced as the angle of aperture of the conical radiation beam is larger.

It is an object of the invention to provide a method in which such artifacts are less pronounced. This object is achieved by means of a computed tomography method in accordance with the invention which includes the steps of:

generating, using a radiation source (S), a conical radiation beam which traverses an examination zone or an object present therein, generating relative motions between the radiation source on the one side and the examination zone or the object on the other side, which relative motions include a rotation about an axis of rotation along a first, closed trajectory and along at least a second trajectory which is identical to the first trajectory but offset in the direction of the axis of rotation, acquiring, while using a detector unit, measuring data which is dependent on the intensity in the radiation beam to the other side of the examination zone during the relative motions, reconstructing a CT image of the examination zone from the measuring values, for the voxels present in an intermediate region between the trajectories there being taken into account measuring values from both trajectories with a weight which is larger as the distance between the voxel and the relevant trajectory is smaller.

As opposed to the known method, in accordance with the invention the measuring values for the voxels present in the intermediate region are used with a weight which is dependent on the distance between the voxel and the two trajectories in such a manner that the weight is greater as the distance between the voxel and the trajectory wherefrom the relevant measuring data was acquired is smaller. The invention is based on the recognition of the fact that said artefacts in the reconstructed CT image are smaller as the angle enclosed by the beams relative to a plane which is perpendicular to the axis of rotation and with which the relevant measuring values are associated is smaller. Therefore, when a larger weight is attached to these measuring values, the described artefacts become less pronounced in the CT image.

In addition to the voxels which are situated in the intermediate region, and hence are irradiated from both trajectories, however, there are also voxels which are irradiated from an angular range of 360° from only one of the trajectories. According to the known method the measuring values of two beams traversing such a voxel from opposite projection directions (the projection direction of a beam is referred to as the orientation parallel to the axis of rotation and the plane containing the relevant beam) are simply summed. In the embodiment disclosed in claim 2, however, these measuring values are weighted in dependence on the cone angle (being the angle enclosed by the relevant beam relative to a plane perpendicular to the axis of rotation), so that the artifacts in the reconstructed CT image are reduced even further.

Claim 3 defines the optimum distance between the two trajectories. In the case of a smaller distance, redundant measuring values would be obtained and in given circumstances the radiation load would be increased, whereas in the case of a larger distance the absorption distribution in the intermediate region could not be reconstructed without loss of image quality. Claim 4 discloses a preferred reconstruction method which requires less calculation effort in comparison with other methods and offers an image of good quality.

A computed tomography apparatus for carrying out the method in accordance with the invention is disclosed in claim 5. The embodiment disclosed in claim 6 results in a reduction of the radiation load (in comparison with a collimator arrangement for generating a radiation beam having a more uniform aperture).

Claim 7 defines a computer program for controlling a computed tomography apparatus as disclosed in claim 5.

Figure 2:
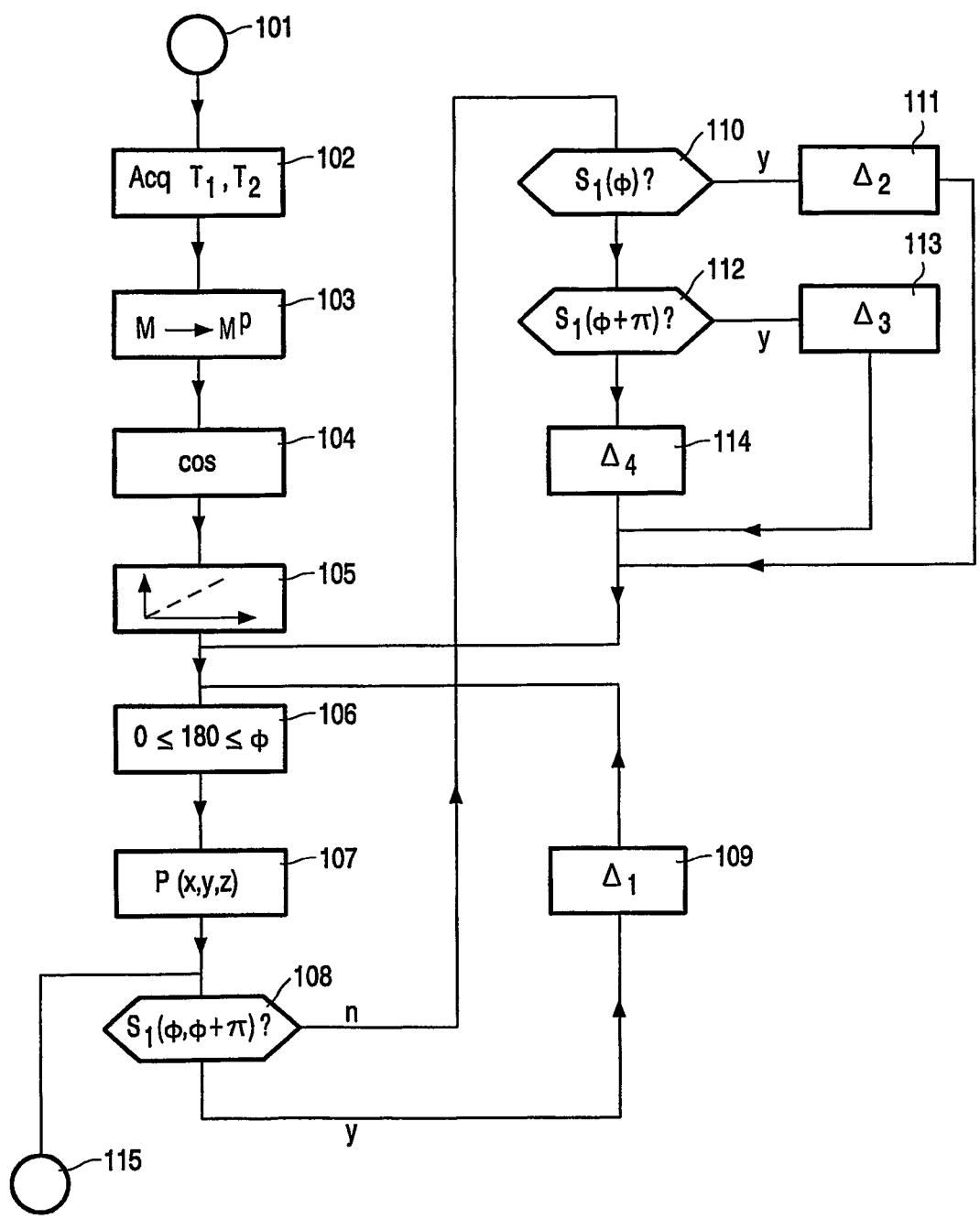
Figure 3:
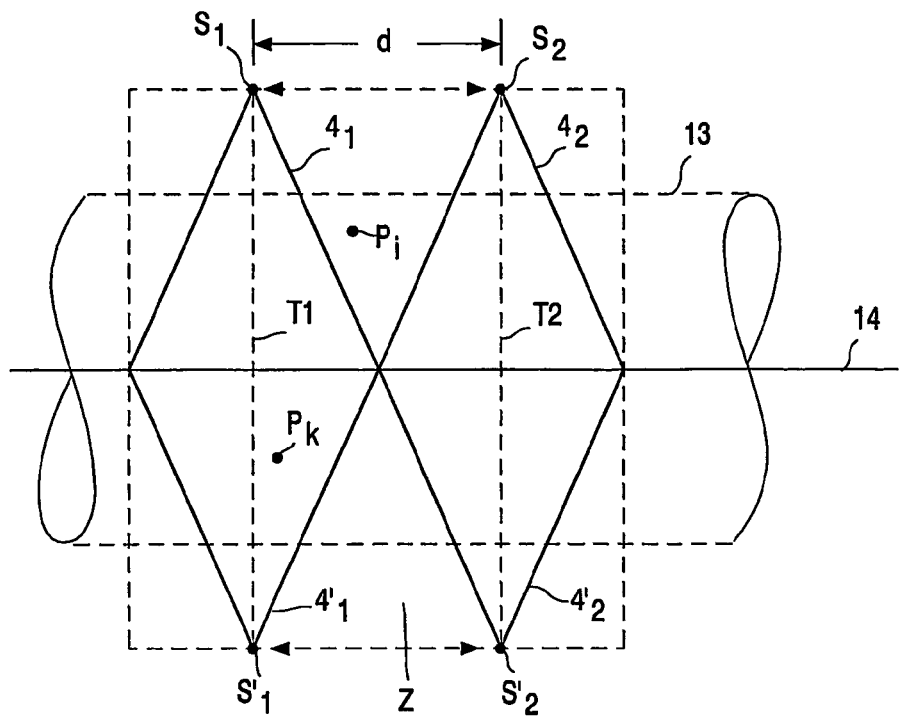
Figure 4:
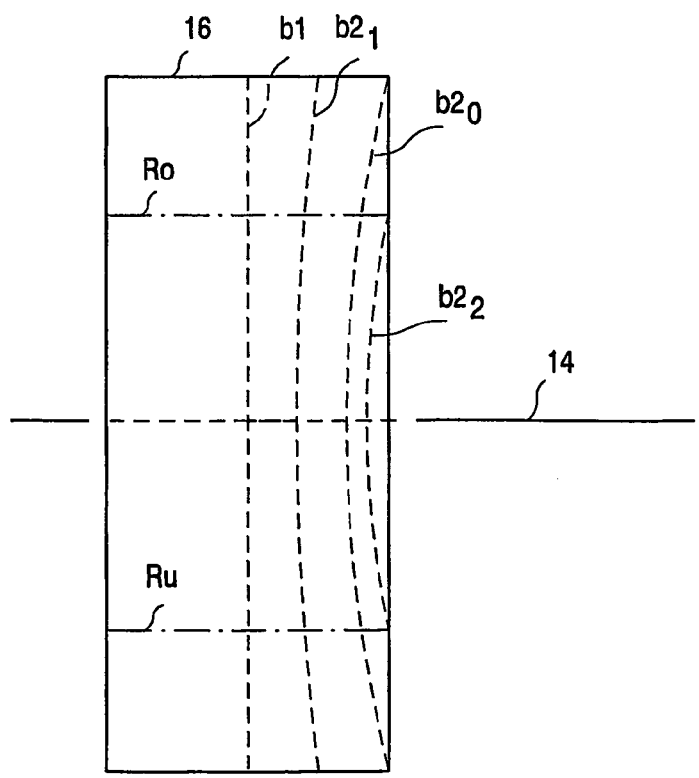
Figure 5:
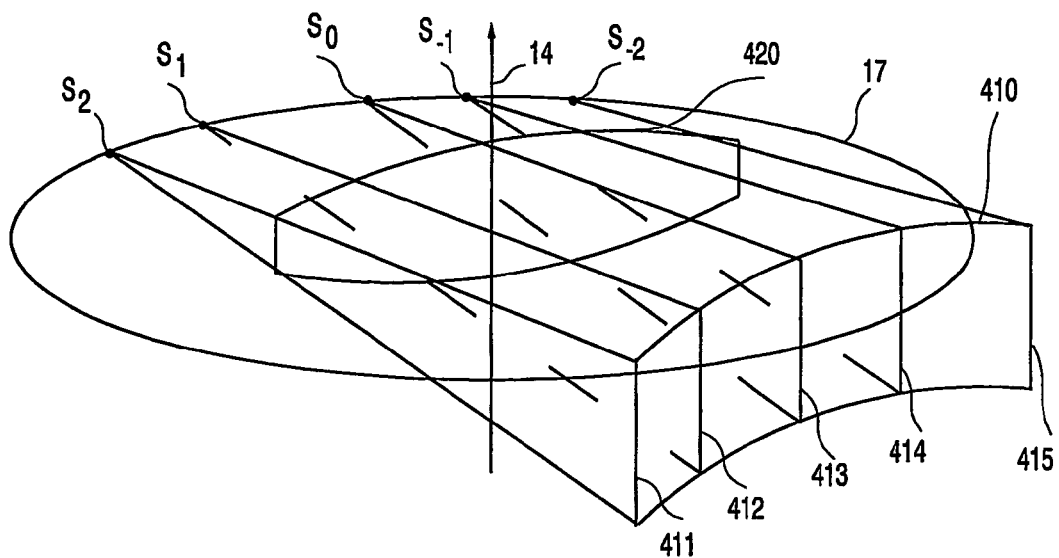
Figure 6:
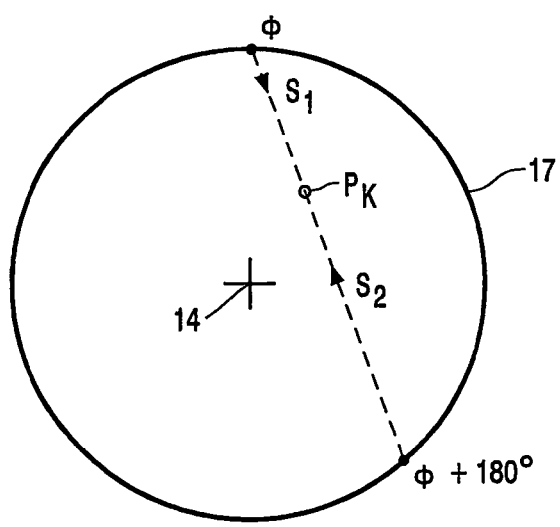
Figure 7A:
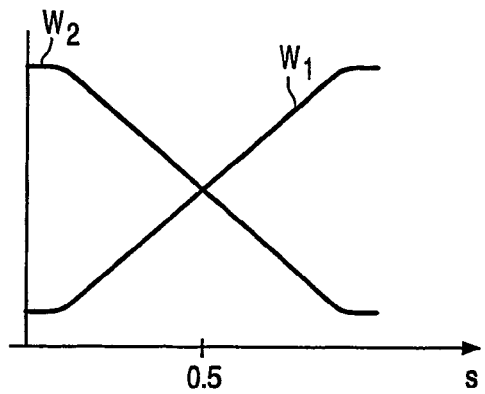
Figure 7B:
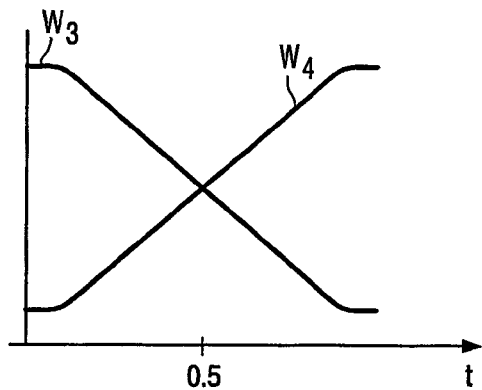
Figure 8:
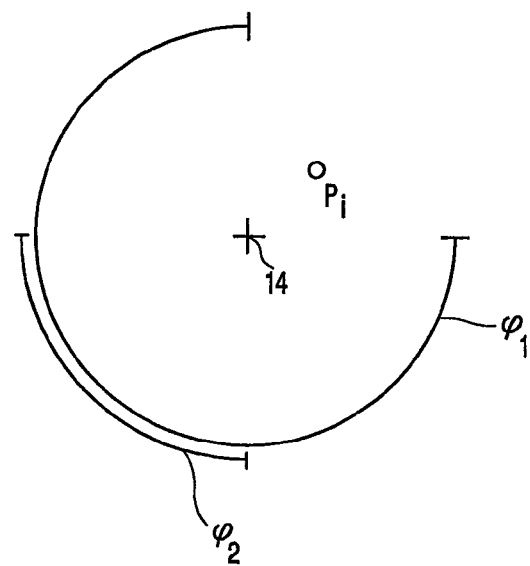

The invention will be described in detail hereinafter with reference to the drawings. Therein:

FIG. 1 shows a computed tomography apparatus which is suitable for carrying out the method in accordance with the invention, FIG. 2 shows a flow chart illustrating the method in accordance with the invention, FIG. 3 shows the situation of the trajectories relative to one another and to the examination zone, FIG. 4 shows the projection of the trajectories on the detector unit, FIG. 5 shows the fan beams formed in parallel planes by a rebinning operation, FIG. 6 shows a trajectory and a voxel, FIGS. 7a and 7b show the dependency of the weight with which the measuring values are used for the reconstruction, and FIG. 8 shows the parts of the trajectories wherefrom a given voxel is irradiated.

The computed tomography apparatus shown in FIG. 1 includes a gantry 1 which is capable of rotation about an axis of rotation 14 which extends in a direction parallel to the z direction of the co-ordinate system shown in FIG. 1. To this end, the gantry is driven by a motor 2 at a preferably constant but adjustable angular speed. A radiation source S, for example, an X-ray source, is mounted on the gantry. The X-ray source is provided with a collimator arrangement 3 which forms a conical radiation beam 4 from the radiation produced by the radiation source S, that is, a radiation beam having a finite dimension other than zero in the z direction as well as in a direction perpendicular thereto (that is, in a plane perpendicular to the axis of rotation).

The radiation beam 4 traverses an examination zone 13 in which an object, for example, a patient on a patient table (both not shown), may be present. The examination zone 13 is shaped as a cylinder. After having traversed the examination zone 13, the X-ray beam 4 is incident on a two-dimensional detector unit 16 which is mounted on the gantry 1 and includes a number of detector rows, each of which includes a plurality of detector elements. The detector rows are situated in planes extending perpendicularly to the axis of rotation, preferably on an arc of a circle around the radiation source S, but they may also have a different shape, for example, they may describe an arc of a circle around the axis of rotation 14 or may be straight. Each detector element struck by the radiation beam 4 delivers a measuring value for a ray of the radiation beam 4 in any position of the radiation source.

The angle of aperture of the radiation beam 4, denoted by the reference $\alpha_{max}$ (the angle of aperture is defined as the angle enclosed by a ray that is situated at the edge of the radiation beam 4 in a plane perpendicular to the axis of rotation relative to a plane defined by the radiation source S and the axis of rotation 14), then determines the diameter of the object cylinder in which the object to be examined is situated during the acquisition of the measuring values. The examination zone 13, or the object or the patient table, can be displaced parallel to the axis of rotation 14 or the z axis by means of a motor 5. Equivalently, however, the gantry could also be displaced in this direction.

When the motors 5 and 2 run simultaneously, the radiation source S and the detector unit 16 describe a helical trajectory relative to the examination zone 13. However, when the motor 5 for the displacement in the z direction is inactive and the motor 2 rotates the gantry, a circular trajectory is obtained for the radiation source S and the detector unit 16 relative to the examination zone 13. For the sake of simplicity only the realization of such a circular trajectory will be considered hereinafter, even though other closed trajectories, for example, elliptical trajectories or trajectories which are inclined relative to the axis of rotation, are also feasible.

The measuring data acquired by the detector unit 16 is applied to an image processing computer 10 which reconstructs the absorption distribution in a part of the examination zone 13 therefrom for display, for example, on a monitor 11. The two motors 2 and 5, the image processing computer 10, the radiation source S and the transfer of the measuring data from the detector unit 16 to the image processing computer 10 are controlled by a control unit 7.

FIG. 2 shows the execution of a measuring and reconstruction method which can be carried out by means of the computed tomography apparatus shown in FIG. 1.

After the initialization in the block 101, the gantry rotates at a constant angular speed. In the step 102 the radiation of the radiation source S is switched on and the measuring values acquired by the detector elements of the detector unit 16 along this first trajectory are stored in a memory of the image processing computer 10. Subsequently, the object, or the examination zone 13, on the one side and the gantry 1 with the radiation source S and the detector 16 on the other side are displaced relative to one another over a distance d while the X-rays are switched off. The gantry subsequently rotates at a constant angular speed again, that is, along a second trajectory. The X-rays are switched on again and the measuring values then acquired by the detector elements of the detector unit 16 are stored in the memory of the image processing computer 10.

FIG. 3 shows the situation of the circular trajectories T1 and T2 along which the radiation source S moves relative to the examination zone 13. For the sake of simplicity it is assumed that the gantry, or the trajectory, has been shifted and that the object stood still; however, this is irrelevant, because the only essential aspect is the relative displacement between the examination zone 13 on the one side and the gantry on the other side. The circular trajectories T1 and T2 appear as (dashed) lines because the axis of rotation 14 is situated in the plane of drawing in the rendition of FIG. 3. Moreover, the radiation source (denoted by a dot) is also shown in the highest position ($S_1$ and $S_2$) and in the lowest position ($S'_1$ and $S'_2$) on each trajectory. The associated radiation beam ($4_1$ and $4_2$ or $4'_1$ and $4'_2$, respectively) is represented in solid lines for each of these positions. The trajectories are situated at the distance d from one another.

Two disc-shaped regions which are defined by the radiation beams $4_1$ and $4_2$ and $4'_1$ and $4'_2$, respectively, can be recognized in FIG. 3. A voxel within such a region, for example, the voxel $P_k$, is struck by X-rays from all positions on the associated trajectory. In this region the absorption distribution, therefore, can be completely reconstructed by means of the measuring values acquired along one of the two trajectories. Therebetween there is situated a region Z. During the travel of the radiation source along the trajectories, the voxels in this intermediate region are temporarily not struck by radiation. For example, the voxel $P_i$ is not struck by radiation from the radiation source positions $S_1$ and $S_2$.

The selection of the distance d in order to ensure that the absorption distribution can also be reconstructed in the region Z will be described in detail hereinafter with reference to FIG. 4. FIG. 4 shows the projection of both trajectories on the detector unit 16. This rendition is based on the assumption that the immaterial trajectories can be projected onto the detector unit (in a geometrical context such a projection, however, can be simply assumed) and that the detector unit 16 is situated on one of the trajectories, for example, on the left-hand trajectory T1.

The projection of the trajectory T1 is denoted by the reference b1. As is shown in FIG. 4, it is identical to the central line of the detector unit, assuming that the detector unit 16 extends symmetrically relative to the trajectory. The trajectory T2 is in principle projected to the right of the trajectory T1 on the detector unit 16 (in the case of a shift to the right), its distance from the projection b1 being larger as the distance d of the trajectory T2 is larger. When the detector unit 16 describes an arc of circle around the radiation source S, as previously assumed, these projections are curved. FIG. 4 shows three different projections for three different distances d between the trajectory T2 and the trajectory T1:

When the distance d is chosen to be such that the projection $b2_1$ is obtained, the entire examination zone between T1 and T2 can be reconstructed; however, this distance is not yet optimum, because it would make the radiation dose unnecessarily high and the reconstructed region unnecessarily short.

The optimum distance $d_{opt}$ (for the case where the complete cross-section of the examination zone 13 is to be imaged) is obtained when the projection of the trajectory T2 extends through the corners of the detector unit, that is, as for the projection $b2_o$. In that case the region between the trajectories can still be imaged and the distance d is larger than in the case of the projection $b2'_1$.

When the distance is chosen to be even larger, the projection $b2_2$ is obtained. This projection no longer intersects the lateral edges of the detector unit (situated at the top and the bottom in FIG. 4), but only the right-hand edge. In this case it is no longer possible to reconstruct the entire cross-section of the examination zone between the two trajectories completely.

However, when an object having a diameter which is smaller than the examination zone 13 is examined and the angle of aperture of the radiation beam 4 is reduced accordingly in a plane perpendicular to the axis of rotation, complete reconstruction of the absorption distribution in the examination zone of reduced diameter may still be possible in this case. A condition to be satisfied in this respect is that the radiation beam 4 should irradiate only the part of the detector unit whose boundaries are denoted by the references Ro and Ru, so that the projection $b2_2$ extends exactly through the corners of the area of the detector unit which is used for the acquisition of measuring data.

The optimum distance $d_{opt}$ for which complete reconstruction of the absorption distribution is possible, therefore, is calculated in conformity with the following formule:

$$d_{opt} = s \tan \gamma \cos \beta$$

Therein, s is the distance between the radiation source S and the axis of rotation, γ is the cone angle (being half the angle of aperture of the radiation beam 4 in a plane containing the axis of rotation 14) and β is the fan angle (being half the angle of aperture of the radiation beam 4 in a plane perpendicular to the axis of rotation 14).

Rebinning of the measuring values is performed in the step 103. For the measuring values acquired along the first trajectory such rebinning may take place already while measuring values are still being acquired along the second trajectory. The measuring values acquired along the two trajectories are resorted and re-interpolated by the rebinning as if they had been formed by means of a different radiation source (a circular radiation source capable of emitting mutually parallel fan beams) and a different detector (a flat, rectangular "virtual" detector containing the axis of rotation 14).

This will be described in detail with reference to FIG. 5. The reference numeral 17 therein denotes one of the two circular trajectories wherefrom the radiation source irradiates the examination zone. The reference numeral 413 denotes a fan-shaped radiation beam which emanates from the radiation source position $S_0$ and whose rays extend in planes containing the axis of rotation 14. The conical radiation beam 4, emitted in the radiation source position $S_0$, may be assumed to be composed of a plurality of flat fan beams which are situated in planes which extend parallel to the axis of rotation 14 and intersect in the radiation source position. FIG. 5 shows only a single one of these fan beams, that is, the fan beam 413. FIG. 5 also shows further fan beams 411, 412 and 414 and 415 which are situated in planes extending parallel to one another and to the axis of rotation 14. The associated radiation source positions $S_2$, $S_1$ and $S_{-1}$ and $S_{-2}$ are occupied by the radiation source S before and after it reaches the radiation source position $S_0$, respectively. All rays in the fan beams 411 . . . 415 have the same projection angle φ (being the angle enclosed by the planes of the fan beam relative to a reference plane parallel to the axis of rotation 14).

The fan beams 411 and 415 define a radiation beam 410 which has a tent-like shape. FIG. 5 shows the region of intersection 420 which occurs when the radiation beam 410 is intersected by a plane which contains the axis of rotation 14 and extends perpendicularly to the planes of the fan beams 411 . . . 415. The parallel rebinning in the step 103 corresponds to a transformation in conformity with the relation $$M(\alpha,\beta,q) \to M^P(\phi,u,v) \quad (1)$$

Therein, M is the set of measuring values obtained for a trajectory after the acquisition and $M^P$ is the set of measuring values resulting from the parallel rebinning. α is an angle which characterizes the position of the radiation source on the trajectory, β is the fan angle, that is, the angle enclosed by a ray associated with the relevant measuring value relative to the radiation source position and the plane containing the axis of rotation 4 q is the level co-ordinate (or the row number), measured in the direction of the axis of rotation, of the detector element delivering the relevant measuring value. φ is the projection angle for which it holds that $$\phi = \alpha + \beta \quad (2)$$

u is the distance between the ray (or the fan beam 411 . . . 415 containing this ray) and the axis of rotation 14 and v is the level co-ordinate of a ray on the region of intersection, that is, the distance between the point in which the relevant ray punctures the region of intersection 420 and the plane of the trajectory 17.

The rays associated with the measuring values $M^P$ define a regular grid in a cubic volume of the (φ, u, v) parameter space. Such parallel rebinning per se is disclosed in EP OS 115028251 which is incorporated herein by way of reference.

As is shown in FIG. 5, the points in which the outer edge rays of the central fan beam 413 puncture the region of intersection 420 are situated further apart, or at a larger distance from one another, than in the outer fan beams 411 or 415. The cubic volume in the three-dimensional (φ, u, v) parameter space, in which the measuring values $M^P$ are defined, however, is defined by said distance of the outer fan beams. The measuring values of rays having a larger u co-ordinate in an absolute sense are no longer required in the further course of the method.

Therefore, the collimator is advantageously constructed in such a manner that as from the beginning the conical radiation beam 4 does not contain rays which extend above the upper edge 161 or below the lower edge 162 of the virtual detector 160. The radiation load for the patient is thus further reduced.

Instead of straight edges extending perpendicularly to the axis of rotation, for this purpose the collimator arrangement 3 should have edges which are curved inwards so that the fan beams which intersect the axis of rotation 14 or are situated at a small distance therefrom would have an angle of aperture (measured in a plane parallel to the axis of rotation) which is smaller than that of fan beams situated at the outer edge of the radiation beam. The outer edge of the surface irradiated on the detector unit 14 by such a radiation beam would then coincide with the projection $b2_0$ (see FIG. 4) which extends through the corner point of the area of the detector unit which is used for the acquisition of measuring data.

Subsequently, in the step 104 the measuring values associated with the individual rays are multiplied by a weighting factor which corresponds to the cosine of the angle enclosed by the ray relative to the plane of the trajectory. If said angle is small, the cosine of this angle will practically always be 1, so that the step 104 can be dispensed with in this case.

In the step 105 the measuring values $M^p$ resulting from the rebinning operation are subjected to one-dimensional filtering with a transfer factor which increases ramp-like as a function of frequency. To this end, use is made each time of measuring values having the same parameters $\phi$ and u, but a different parameter v. This filtering is repeated for all other values of $\phi$ and u.

The measuring values obtained after the rebinning and the filtering are subsequently used for the reconstruction of the absorption distribution in the examination zone by way of a backprojection.

After the selection of a projection angle $\phi$ in the step 106, a voxel P(x, y, z) is selected in the step 107. In the step 108 it is then checked whether there are rays which emanate from the first trajectory and extend through the voxel P(x, y, z) in the projection directions $\phi$ and $\phi+180°$.

If this is the case, in the step 109 for the relevant voxel (for example, the voxel $P_k$ in FIG. 3) a contribution $\Delta_1$ is derived from the filtered measuring values associated with these rays. In this respect reference is made to FIG. 6 which shows the first trajectory (17) in a plane perpendicular to the axis of rotation as well as the projection of the voxel $P_k$ parallel to the axis of rotation. The two radiation source positions on the trajectory wherefrom the voxel was irradiated from the directions $\phi$ and $\phi+180°$, respectively, are also shown. The two radiation source positions usually are not diametrically oppositely situated, but the projection of the voxel is situated on the connecting line of the two radiation source positions. The distance between the radiation source position $\phi$ and the projection of $P_k$ is denoted by the reference $s_1$ and the distance between the projection of $P_k$ and the radiation source position $\phi+180°$ is denoted by the reference $s_2$. The contribution $\Delta_1$ is calculated in conformity with the formule:

$$\Delta_1 = c(w_1(s) \cdot F_1(\phi) + w_2(s) \cdot F_1(\phi+180°)) \quad (3)$$

Therein, c is a constant, $F_1(\phi)$ and $F_1(\phi+180°)$ are the filtered measuring values for the rays traversing the voxel from the projection directions $\phi$ and $\phi+180°$, respectively, and $w_1(s)$ and $w_2(s)$ are complementary weighting factors which are dependent on a parameter s for which it holds that:

$$s = \frac{s_1}{s_1 + s_2} \quad (4)$$

$s_1$ and $s_2$ are the length of the segments between the projection of the voxel $P_k$ and the trajectory 17.

FIG. 7a shows the variation of the weighting factors $w_1$ and $w_2$ as a function of s. For small values of s, $w_2$ is larger than $w_1$, whereas for s values approximately equal to 1 the value $w_1$ is larger than $w_2$. Therebetween the weighting factors increase and decrease monotonously. Their sum (for the same value s) is always constant. For the constellation shown in FIG. 6 this means that the filtered measuring value from the radiation source position $\phi$ enters the equation (3) with a weight which is smaller than that of the filtered value $F_1(\phi+180°)$. This is because $s_1$ is smaller than $s_2$, so that the cone angle for the ray associated with the measuring value $F_1(\phi)$ is larger than that for the ray which is associated with the measuring value $F_1(\phi+180°)$. Therefore, the artifact which is caused by the fact that the voxel $P_k$ is not situated in the plane of the trajectory is less than for the ray associated with the value $F_1(\phi+180°)$, so that because of this weighting this measuring value is emphasized relative to the measuring value $F_1(\phi)$.

When the interrogation taking place in the step 108 is negative, that is, when the voxel selected in the step 107 is not completely irradiated from the first trajectory, it is checked in the step 110 whether there is a ray which traverses the relevant voxel in the projection direction $\phi$. The existence of such a ray means that the voxel is situated in the intermediate region Z such as, for example, the voxel $P_i$ in FIG. 3. This case is illustrated in FIG. 8 which shows the axis of rotation 14, extending perpendicularly to the plane of drawing, and the pixel $P_i$. This figure also shows the arcs $\sigma_1$ and $\sigma_2$ wherefrom the radiation source can irradiate the relevant voxel on the trajectories T1 and T2, respectively. It appears that the voxel $P_i$ cannot be irradiated from the radiation source positions situated nearer to this point. FIG. 3 also shows that the point $P_i$ can be irradiated by the radiation beam $4'_1$ from the lower radiation source positions, but not by the radiation beam $4_1$ which is emitted in the radiation source position $S_1$ which is situated nearer to the point $P_i$.

In the step 111 a contribution $\Delta_2$ is calculated for this voxel in conformity with the relation:

$$\Delta_2 = c(w_3(t) \cdot F_1(\phi) + w_4(t) \cdot F_2(\phi)) \quad (5)$$

Therein, $F_2(\phi)$ is the filtered value for a ray which traverses the selected voxel from the second trajectory at the projection angle $\phi$. $w_3(t)$ and $w_4(t)$ are weighting factors which are dependent on a parameter t, where t is the distance between the voxel and the plane of the first trajectory, divided by the distance d between the two trajectories. The variation of the weighting factors $w_3(t)$ and $w_4(t)$ is shown in FIG. 7b and corresponds essentially to the variation shown in FIG. 7a. If the voxel is situated nearer to the plane of the first trajectory than to the plane of the second trajectory, $w_3$ is larger than $w_4$ so that the measuring value $F_1(\phi)$ enters the reconstruction with a weight which is higher than that of the measuring value $F_2(\phi)$. In this case the measuring value $F_1$ is associated with a ray which encloses an angle relative to the plane of the trajectories which is smaller than that enclosed by the ray associated with the value $F_2(\phi)$, so that the artifacts produced are smaller.

If the check 110 is negative, a third check takes place in the step 112. Therein it is determined whether there is a ray which traverses the selected voxel at an angle of $\phi+180°$ from the first trajectory. If this is the case, the voxel must also be situated in the intermediate region Z, be it in a sector other than the voxel shown. In this case in the step 113 a contribution $\Delta_3$ is calculated in conformity with the relation:

$$\Delta_3 = c(w_3(t) \cdot F_1(\phi+180°) + w_4(t) \cdot F_2(\phi+180°)) \quad (6)$$

If the result of all three checks 108, 110 and 112 is negative, the voxel can be situated only within the region which is fully irradiated from the second trajectory. In that case there is determined a contribution $\Delta_4$ which is calculated, analogously to the equation 3, in conformity with the relation:

$$\Delta_4 = c(w_1(s) \cdot F_2(\phi) + w_2(s) \cdot F_2(\phi+180°)) \quad (7)$$

The program loop consisting of the steps 106 to 114 is repeated a number of times until for each voxel a contribution has been determined from each projection angle $\phi$ in a range from 0 to 180°, said contribution being accumulated with the previously determined contributions. The method is then terminated in the step 115.

When the region of relevance to the examination is larger, the measuring values can be reconstructed along more than two trajectories. The region between two neighboring trajectories is then reconstructed each time as described with reference to FIG. 2.

Other reconstruction methods in which the rebinning operation is performed in a different manner are also feasible. However, for the reconstruction of the absorption distribution in the intermediate region it will then again be necessary to take into account measuring values acquired along both trajectories.

The invention claimed is:

1. A computed tomography method which includes the steps of
   generating, using a radiation source, a conical radiation beam which traverses an examination zone or an object present therein,
   generating relative motions between the radiation source on the one side and the examination zone or the object on the other side, which relative motions include a rotation about an axis of rotation along a first, closed trajectory and along at least a second trajectory which is identical to the first trajectory but offset in the direction of the axis of rotation,
   acquiring, while using a detector unit, measuring values which are dependent on the intensity in the radiation beam to the other side of the examination zone during the relative motions,
   reconstructing a CT image of the examination zone from the measuring values, for the voxels present in an intermediate region between the trajectories there being taken into account measuring values from both trajectories with a weight which is larger as the distance between the voxel and the relevant trajectory is smaller.

2. A computed tomography method as claimed in claim 1, in which for the reconstruction for a voxel the measuring values of two rays which emanate from the same trajectory and traverse the relevant voxel from opposite projection directions are taken into account with a weight which increases as the cone angle increases.

3. A computed tomography method as claimed in claim 1, characterized in that the distance between the trajectories is chosen in such a manner that the projections of one of the two trajectories always extend through at least one corner point of the area of the detector unit which is used for the acquisition of measuring data.

4. A computed tomography method as claimed in claim 1, in which the reconstruction includes the following steps:
   a) rebinning of the measuring values so as to form a number of groups, each group including a plurality of planes which extend parallel to one another and to the axis of rotation and which contain a respective fan beam,
   b) one-dimensional filtering of the data produced by the rebinning operation for each group in the direction perpendicular to the direction of the planes,
   c) reconstruction of the spatial distribution of the absorption by backprojection of the filtered data of a plurality of groups while taking into account filtered data from both trajectories for the backprojection in the intermediate region.

5. A computed tomography apparatus for carrying out the method claimed in claim 1, including
   a radiation source for generating a conical radiation beam which traverses an examination zone or an object present therein,
   a detector unit which is coupled to the radiation source,
   a drive arrangement for rotating and/or displacing an object present in the examination zone and the radiation source relative to one another about an axis of rotation and/or parallel to the axis of rotation,
   a reconstruction unit for reconstructing the spatial distribution of the absorption within the examination zone from the measuring values acquired by the detector unit, and
   a control unit for controlling the radiation source, the detector unit, the drive arrangement and the reconstruction unit in conformity with the following steps:
   generating, using a radiation source, a conical radiation beam which traverses an examination zone or an object present therein,
   generating relative motions, between the radiation source on the one side and the examination zone or the object on the other side, which relative motions include a rotation about an axis of rotation along a first, closed trajectory and along at least a second trajectory which is identical to the first trajectory but offset in the direction of the axis of rotation,
   acquiring, while using a detector unit, measuring values which are dependent on the intensity in the radiation beam to the other side of the examination zone during the relative motions,
   reconstructing a CT image of the examination zone from the measuring values, for the voxels present in an intermediate region between the trajectories there being taken into account measuring values from both trajectories with a weight which is larger as the distance between the voxel and the relevant trajectory is smaller.

6. A computed tomography apparatus as claimed in claim 5, including a collimator arrangement which is connected to the radiation source and whose edges which are mutually offset in the direction of the axis of rotation are shaped in such a manner that the conical radiation beam has an aperture which is smaller at its center than at its edges.

7. A computer program for a control unit for controlling a radiation source, a detector unit, a drive arrangement and a reconstruction unit of a computed tomography apparatus for carrying out the method claimed in claim 1 as follows:
   generating, using a radiation source, a radiation beam which traverses an examination zone or an object present therein,
   generating relative motions between the radiation source on the one side and the examination zone or the object on the other side, which relative motions include a rotation about an axis of rotation along a first, closed trajectory and along at least a second trajectory which is identical to the first trajectory but offset in the direction of the axis of rotation,
   acquiring, while using a detector unit, measuring values which are dependent on the intensity in the radiation beam to the other side of the examination zone during the relative motions,
   reconstructing a CT image of the examination zone from the measuring values, for the voxels present in an intermediate region between the trajectories there being taken into account measuring values from both trajectories with a weight which is larger as the distance between the voxel and the relevant trajectory is smaller.

* * * * *